(12) United States Patent
Sluti et al.

(10) Patent No.: US 11,980,355 B2
(45) Date of Patent: May 14, 2024

(54) TISSUE TRACTION BANDS AND METHODS FOR TISSUE TRACTION

(71) Applicant: Boston Scientific Scimed, Inc., Maple Grove, MN (US)

(72) Inventors: Anne Sluti, Watertown, MA (US); Talha Riaz, Framingham, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 458 days.

(21) Appl. No.: 15/930,620

(22) Filed: May 13, 2020

(65) Prior Publication Data

US 2020/0360006 A1 Nov. 19, 2020

Related U.S. Application Data

(60) Provisional application No. 62/908,972, filed on Oct. 1, 2019, provisional application No. 62/848,815, filed on May 16, 2019.

(51) Int. Cl.
*A61B 17/02* (2006.01)
*A61B 1/00* (2006.01)
(Continued)

(52) U.S. Cl.
CPC ...... *A61B 17/0293* (2013.01); *A61B 1/00135* (2013.01); *A61B 1/0014* (2013.01);
(Continued)

(58) Field of Classification Search
CPC ...... A61B 2017/00269; A61B 17/0218; A61B 17/128; A61B 17/1285; A61B 2017/0034;
(Continued)

(56) References Cited

U.S. PATENT DOCUMENTS 5,379,759 A * 1/1995 Sewell, Jr. ......... A61B 17/0218
600/207
5,445,167 A * 8/1995 Yoon .................. A61B 17/0057
606/139

(Continued)

FOREIGN PATENT DOCUMENTS

CN 107928721 A * 4/2018 ......... A61B 17/0218
CN 109350147 A * 2/2019 ......... A61B 17/0218
(Continued)

OTHER PUBLICATIONS

International Search Report and Written Opinion for the International Patent Application No. PCT/US2020/032583, mailed Jul. 30, 2020, 17 pages.

(Continued)

*Primary Examiner* — Julianna N Harvey
*Assistant Examiner* — Anna V. Little
(74) *Attorney, Agent, or Firm* — Seager, Tufte & Wickhem, LLP

(57) ABSTRACT

The present disclosure relates generally to the field of medical devices. In particular, the present disclosure relates to a tissue traction device, e.g., for an endoscopic procedure such as endoscopic tissue dissection. For example, a tissue traction device may include a traction band having a first end, a second end, a length therebetween and extending along a longitudinal axis. A first attachment member may extend from the first end of the traction band. A second attachment member may be associated with the body between the first end and the second end of the traction band. A third attachment member may extend from the second end of the traction band.

20 Claims, 8 Drawing Sheets

(51) Int. Cl.
 *A61B 17/00* (2006.01)
 *A61B 90/00* (2016.01)
(52) U.S. Cl.
 CPC ... *A61B 17/0218* (2013.01); *A61B 2017/00292* (2013.01); *A61B 2017/00818* (2013.01); *A61B 2090/0807* (2016.02)
(58) Field of Classification Search
 CPC ...... A61B 2017/00818; A61B 17/0293; A61B 2017/0287; A61B 2017/00234; A61B 17/0206; A61B 1/0014; A61B 17/02
 See application file for complete search history.

(56) References Cited

U.S. PATENT DOCUMENTS

| | | | |
|---|---|---|---|
| 5,582,577 A * | 12/1996 | Lund | A61B 17/0218 600/233 |
| 5,749,879 A * | 5/1998 | Middleman | A61B 18/082 606/139 |
| 5,803,903 A * | 9/1998 | Athas | A61B 17/0293 600/231 |
| 7,018,332 B1 * | 3/2006 | Masson | A61B 17/02 600/206 |
| 8,062,311 B2 | 11/2011 | Litscher et al. | |
| 8,114,018 B2 * | 2/2012 | Park | A61B 17/02 600/206 |
| 9,451,941 B2 * | 9/2016 | Scott | A61B 17/083 |
| 10,952,717 B2 | 3/2021 | Salazar et al. | |
| 2004/0050395 A1 * | 3/2004 | Ueda | A61B 34/73 128/899 |
| 2007/0073322 A1 * | 3/2007 | Mikkaichi | A61B 17/0469 606/153 |
| 2007/0250116 A1 * | 10/2007 | Raju | A61B 17/0218 606/216 |
| 2009/0276038 A1 * | 11/2009 | Tremulis | A61B 17/0401 623/2.11 |
| 2012/0078057 A1 * | 3/2012 | Scott | A61B 17/04 600/201 |
| 2012/0316593 A1 * | 12/2012 | Kim | A61B 17/0218 606/185 |
| 2015/0201934 A1 * | 7/2015 | Smith | A61B 17/105 606/151 |
| 2015/0257758 A1 * | 9/2015 | Qadeer | A61B 17/0644 606/219 |
| 2015/0351855 A1 * | 12/2015 | Lee | A61B 17/0218 600/204 |
| 2016/0143634 A1 * | 5/2016 | Scott | A61B 17/0466 600/37 |
| 2017/0095363 A1 * | 4/2017 | Hiernaux | A61B 17/0401 |
| 2018/0035997 A1 * | 2/2018 | Smith | A61B 17/083 |
| 2018/0116778 A1 * | 5/2018 | Chin | A61B 17/3423 |
| 2018/0263613 A1 * | 9/2018 | Wik | A61B 17/02 |
| 2018/0263614 A1 * | 9/2018 | Lee | A61B 17/0206 |
| 2018/0279869 A1 * | 10/2018 | Wales | A61B 1/32 |
| 2019/0099172 A1 * | 4/2019 | Wales | A61B 17/083 |
| 2019/0133591 A1 * | 5/2019 | Dobashi | A61B 17/06166 |
| 2019/0216463 A1 * | 7/2019 | Dobashi | A61B 17/1285 |
| 2020/0129181 A1 | 4/2020 | Carrillo et al. | |
| 2020/0360006 A1 | 11/2020 | Sluti et al. | |
| 2020/0360023 A1 | 11/2020 | Bagley et al. | |

FOREIGN PATENT DOCUMENTS

| | | |
|---|---|---|
| EP | 1598020 A1 | 11/2005 |
| JP | 2005103107 A | 4/2005 |
| JP | 200862004 A | 3/2008 |
| WO | 2010099327 A1 | 9/2010 |
| WO | 2013041960 A1 | 3/2013 |
| WO | 2018156768 A1 | 8/2018 |

OTHER PUBLICATIONS

Takeda T et al., Traction Device to Remove an Adenoma in the Appendiceal Orifice by Endoscopic Submucosal Dissection, Endoscopy 2013; 45:E239-E240.

Sakamoto N. et al., The Facilitation of a New Traction Device (S-O Clip) Assisting Endoscopic Submucosal Dissection For Superficial Colorectal Neoplasms, Endoscopy 2008; 40:E94-95.

Sakamoto N. et al., Endoscopic Submucosal Dissection of Large Colorectal Tumors by Using a Novel Spring-Action S-O Clip for Traction (with video), Gastrointestinal Endoscopy 69(7):1370-74 (2009).

* cited by examiner

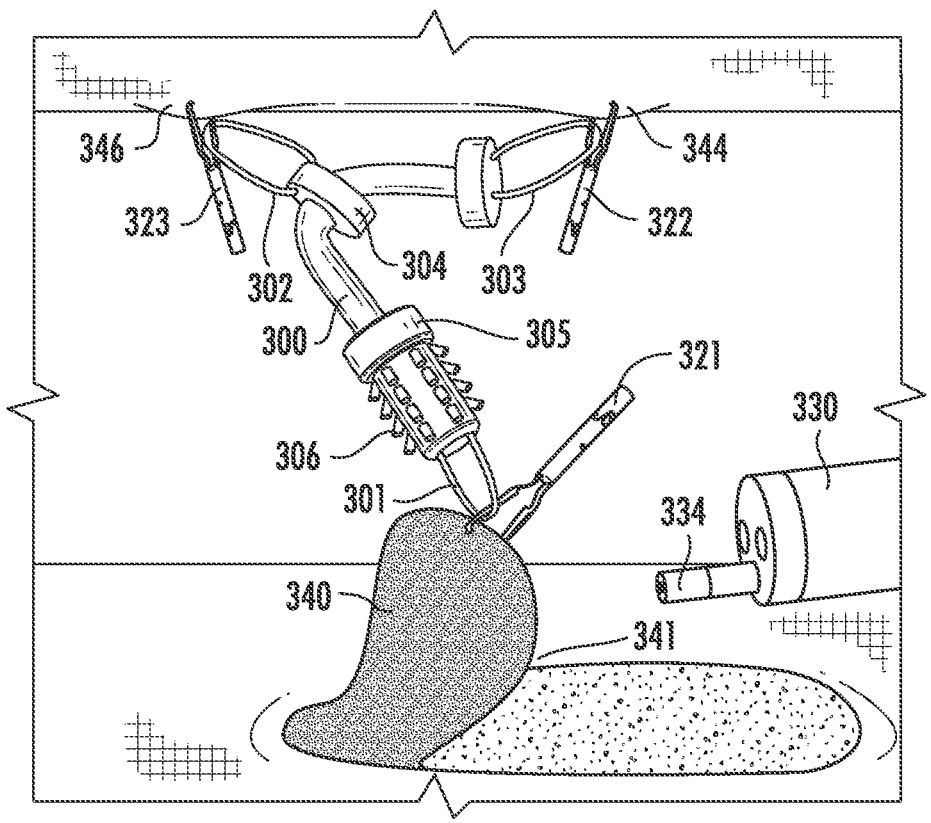
FIG. 3D
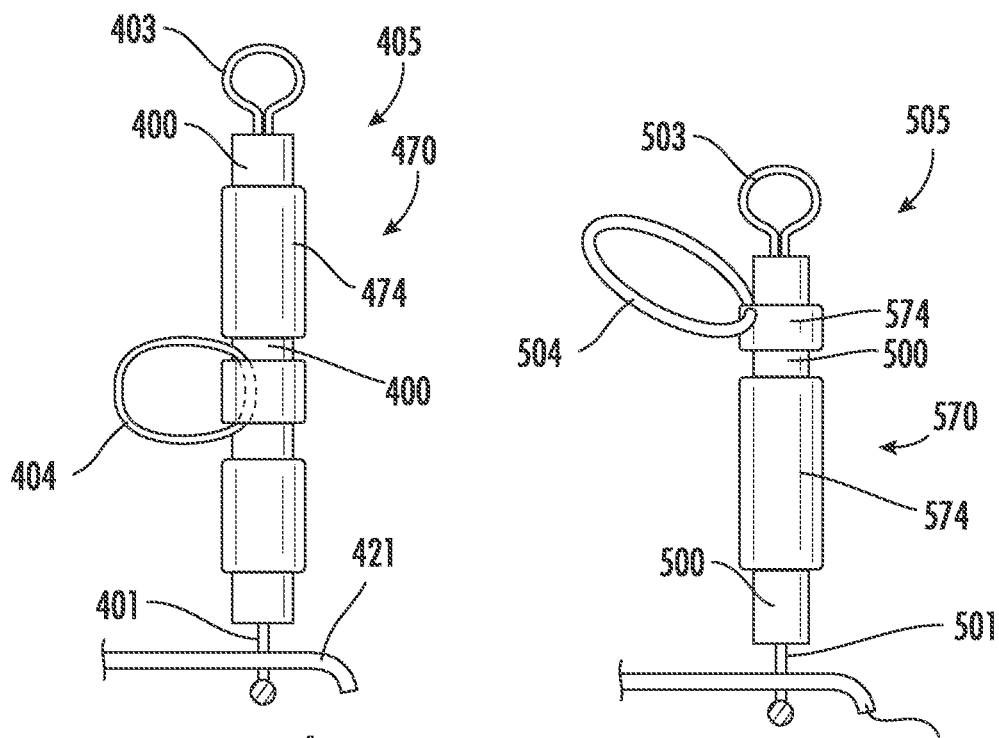
FIG. 4
FIG. 5

TISSUE TRACTION BANDS AND METHODS FOR TISSUE TRACTION

CROSS-REFERENCE TO RELATED APPLICATION

The present application claims the benefit of priority under 35 U.S.C. § 119 to U.S. Provisional Patent Application 62/908,972, filed Oct. 1, 2019; and U.S. Provisional Patent Application 62/848,815, filed May 16, 2019, both of which applications are incorporated herein by reference in their entireties for all purposes.

FIELD

The present disclosure relates generally to the field of medical devices. In particular, the present disclosure relates to tissue retraction/traction devices, e.g., for endoscopic procedures such as tissue dissection, and related methods of use thereof.

BACKGROUND

A component of accurately and efficiently performing an endoscopic tissue resection/dissection procedure is the ability to maintain traction as the boundaries of the target tissue are dissected. Traction systems may be unable to maintain or adjust tension applied to the target tissue, possibly obstructing a medical professional's view of the target tissue and/or interfering with accessory tools. These complications may directly contribute to increased procedures time, complexity and risk of perforation or bleeding.

It is with these considerations in mind that the improvements in the tissue retraction devices and related methods of use of the present disclosure may be useful.

SUMMARY

The present disclosure, in its various aspects, is directed generally to medical devices, and more specifically to tissue retraction/traction devices, retraction/traction methods, and related delivery systems. Embodiments according to the present disclosure, including as described herein, may decrease complications around endoscopic procedures such as tissue resection/dissection procedures, such as visualization, procedure time, and procedure complexity. In an aspect, a tissue retraction/traction device may include a traction band having a first end, a second end, and a length therebetween extending along a longitudinal axis. The traction band may comprise a compliant or semi-compliant material. A body may be disposed at the first end of the traction band. At least one protrusion may be disposed on the body. A ring may be disposed about and positioned along the length of the traction band. A first attachment member may extend from the first end of the traction band. A second attachment member may be associated with the body between the first end and the second end of the traction band. A third attachment member may extend from the second end of the traction band. The ring may be slidable along the length of the traction band. The second attachment member may extend from the ring.

In various embodiments described here or otherwise, a ring may be disposed about and positioned along the length of the traction band. A body may be disposed at the first end of the traction band. At least one protrusion may be disposed on the body. The ring may be fixed to the traction band. The protrusion may extend at an angle radially away from the longitudinal axis of the traction band. A plurality of protrusions may be arranged circumferentially about the body. The first attachment member, the second attachment member, and the third attachment member may each be selected from a loop, a hook, an anchor, a barb, an eyelet, or a clip, or combinations thereof. A first stopper may be disposed about the traction band between the ring and the first end. The first stopper may be configured to prevent the ring from translating along the length of the traction band to the first attachment member. A second stopper may be disposed about the traction band between the ring and the second end. The second stopper may be configured to prevent the ring from translating along the length of the traction band to the second attachment member. The device may include at least a first and second protrusion. The second protrusion may be disposed on the body between the first protrusion and a first end of the body. At least one of the first attachment member, the second attachment member, and the third attachment member may include a visual indicator that is visually distinguishable from the remaining members.

In an aspect, a tissue retraction/traction system may include a tissue retraction/traction device. The tissue retraction/traction device may include a traction band having a first end, a second end, and a length therebetween. The device may include a body coupled to the traction band. At least one protrusion may be disposed on the body. A first attachment member may extend from the body. A second attachment member may extend from the traction band. The second attachment member may be slidable along the band. A third attachment member may extend from the second end of the traction band. A first tissue fastener may be engageable with the first attachment member. A second tissue fastener may be engageable with the second attachment member. A delivery catheter may be configured to deliver the traction band, the first tissue fastener, and the second tissue fastener.

In various embodiments, a grasping tool may be configured to engage and move the third attachment member into engagement with the protrusion. The first tissue fastener may be configured to reversibly engage the first attachment member with a first target tissue location. The second tissue fastener may be configured to reversibly engage a second target tissue location engaged to the second attachment member. A third tissue fastener may be engageable with the third attachment member. The body may be disposed at the first end of the traction band. The tissue retraction/traction device and the first tissue fastener may be pre-loaded prior to use within the delivery catheter. The first tissue fastener may be engaged with the first attachment member. A ring may be disposed about and positioned along the length of the traction band. The second attachment member may extend from the ring.

In various embodiments, an attachment member may be associated with an overtube or a segment of an overtube positioned over the traction band between the first end and the second end thereof. One or more attachment members may be coupled to at least one of the overtube segments. In various embodiments, an attachment member may be coupled to more than one or each segment of the segmented overtube.

In an aspect, a method of retracting tissue may include delivering a tissue traction device to a target tissue. A first attachment member from a first end of the tissue traction device may be attached to the target tissue. A second attachment member from a length of the tissue retraction/traction device may be attached to an anchoring portion of tissue. A procedure may then be performed on the target tissue. In some embodiments, the target tissue may be resected. A third attachment member extending from a second end of the tissue retraction/traction device may be engaged to a first protrusion extending from the tissue retraction/traction device. A tension, and/or length of the tissue retraction/traction device, applied by the tissue retraction/traction device to the target tissue may be adjusted.

In various embodiments, a third attachment member may be engaged from a second end of the tissue retraction/traction device to a first protrusion extending from the tissue retraction/traction device or to another anchoring portion of tissue. The third attachment member may be moved from the first protrusion to a second protrusion extending from the tissue retraction/traction device. The first attachment member and the target tissue may be engaged with a first fastener. The second attachment member and the anchoring portion of tissue may be engaged with a second fastener. An area of access beneath the target tissue may be visualized and a position of the third attachment member may be adjusted based on the visualized area of access.

In various embodiments, a first attachment member from a first end of the tissue traction device may be attached to the target tissue. A second attachment member from a second end of the tissue retraction/traction device may be attached to a first anchoring portion of tissue. A procedure may then be performed on the target tissue. In some embodiments, the target tissue may be resected. A third attachment member extending from the tissue retraction/traction device between the first and second ends of the tissue retraction/traction device may be engaged to a second anchoring portion of tissue spaced apart from the first anchoring portion of tissue. A tension, and/or length of the tissue retraction/traction device, applied by the tissue retraction/traction device to the target tissue may be adjusted.

BRIEF DESCRIPTION OF THE DRAWINGS

Non-limiting embodiments of the present disclosure are described by way of example with reference to the accompanying figures, which are schematic and not intended to be drawn to scale. For example, devices may be enlarged so that detail is discernable, but is intended to be scaled down in relation to, e.g., fit within a working channel of a delivery catheter or endoscope. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIG. 3D illustrates the tissue traction device of FIGS. 1 and 3A-3C with an attachment member engaged by a fastener with a second anchoring portion of tissue in accordance with an embodiment of the present disclosure.

FIG. 4 illustrates another embodiment of a tissue traction device, with a first embodiment of an attachment member, in accordance with the present disclosure.

FIG. 5 illustrates an embodiment of a tissue traction device similar to the tissue traction device of FIG. 4, but showing a second embodiment of an attachment member, in accordance with the present disclosure.

Figure 1:
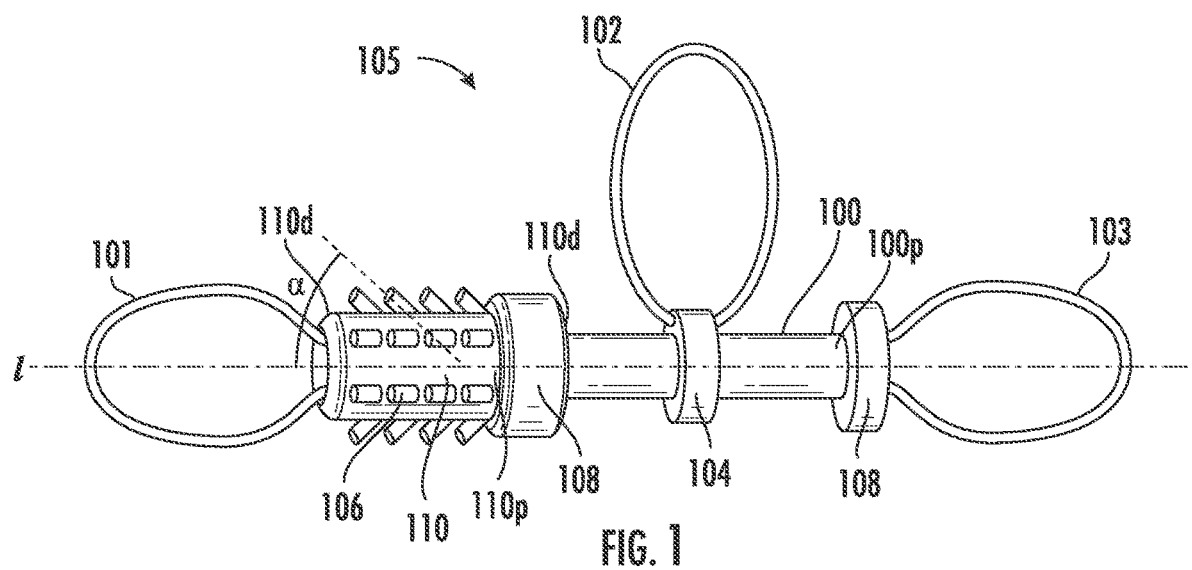
FIG. 1 illustrates a tissue traction device, in accordance with an embodiment of the present disclosure.

It is noted that the drawings are intended to depict only typical or exemplary embodiments of the disclosure. Accordingly, the drawings should not be considered as limiting the scope of the disclosure. The disclosure will now be described in greater detail with reference to the accompanying drawings.

DETAILED DESCRIPTION

As used herein, "proximal end" refers to the end of a device that lies closest to the medical professional along the device when introducing the device into a patient, and "distal end" refers to the end of a device or object that lies furthest from the medical professional along the device during implantation, positioning, or delivery.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified. The recitation of numerical ranges by endpoints includes all numbers within that range, including the endpoints (e.g., 1 to 5 includes 1, 1.5, 2, 2.75, 3, 3.80, 4, and 5).

The detailed description should be read with reference to the drawings, which are not necessarily to scale, depict illustrative embodiments, and are not intended to limit the scope of the invention.

A number of medical procedures, including along the digestive and/or biliary tract, utilize medical devices to access tissue intended for removal (e.g., "target tissue") within the body. For example, in some current medical procedures (e.g., endoscopic submucosal dissection ESD, Peroral Endoscopic Myotomy (POEM), cholecystectomy, Video-Assisted Thoracoscopic Surgery (VATS)), physicians may utilize an endoscope or similar medical device to access and remove diseased lesions. Further, as part of such procedures, a physician may utilize an endoscope capable of both accessing the target tissue site while also permitting a resecting device to be deployed therethrough to resect target tissue. Additionally, in some instances, an endoscope may incorporate features which assist the physician in visualizing and performing the tissue dissection/resection procedure. For example, some endoscopes may include a light and/or camera designed to illuminate and/or visualize the body lumen as the endoscope is navigated and positioned adjacent to the target tissue site. Additionally, some endoscopes may also include a lumen (e.g., a working channel) through which a resecting device, grasping member, delivery catheter for the same, or other accessory devices, may be deployed and utilized. Additional visualization methods may be alternatively or additionally employed, e.g., fluoroscopy.

While physicians are becoming more proficient at resecting diseased lesions from within the body (e.g., within the digestive tract, abdominal cavity, thoracic cavity, etc.), present retraction methods may continue to be inefficient and frustrating to the physician. For example, in some instances poor visualization and poor ability to engage and manipulate tissue may result in a prolonged tissue dissection procedure. An aspect of ESD that may be difficult is the positioning and maneuvering (e.g., retraction) of a resected tissue flap during and after resecting. In some ESD procedures, physicians may use separate devices to provide a means of tissue traction. Such procedures may include multiple device exchanges and extended procedure times. Such systems may be unable to maintain or adjust tension applied to the target tissue, and/or may maintain or adjust tension applied to the target tissue in an inefficient or inconsistent manner.

Referring to FIG. 1, a tissue retraction/traction (such terms being used in the alternative, or simply referenced as "traction" for the sake of simplicity and without intent to limit) device 105 is illustrated according to an embodiment of the present disclosure, which may be inserted through a catheter or endoscope for deployment to apply tension to a target tissue. The traction device 105 includes a traction band 100 having a first end 100d, a second end 100p, and a length therebetween extending along a longitudinal axis l. A body 110 may be disposed at the first end 100d of the traction band 100. In embodiments, the body 110 may be fixedly coupled to the traction band 100. In some embodiments, the body 110 may be integrally formed with the traction band 100. In other embodiments, the body 110 may be detachably coupled to the traction band 100. In some embodiments, the body 110 may be flexible, semi-rigid, or rigid. In some embodiments, the body 110 may be optional and not included as part of the band 100.

A first attachment member 101 extends from a first end 110d of the body 110. In embodiments, the first attachment member 101 may extend substantially along the longitudinal axis l and outward from the first end 110d of the body 110. A second attachment member 102 extends from a ring 104 about the traction band 100 along its length. In embodiments, the second attachment member 102 may extend radially outward and away from the traction band 100, e.g., substantially perpendicular to the longitudinal axis l. In use, the second attachment member 102 may be positionable at an angle relative to the longitudinal axis l. The ring 104 may be fixed to the traction band 100 (e.g., such as being crimped thereto or otherwise fixed, such as by adhesive), or the ring 104 may be slidable along the length of the traction band 100 and rotatable about the longitudinal axis l, e.g., to allow the traction band 100 to be adjusted with respect to the ring 104 and the second attachment member 102. Stopper members 108 may be fixedly attached to the traction band 100 (e.g., such as being crimped thereto or otherwise fixed, such as by adhesive) on either side of the ring 104 such that translation of the ring 104 sliding along the length of the traction band 100 is prevented by the stopper members 108 from extending past the stopper members 108 and off the traction band 100. A stopper member 108 may connect the first end 100d of the traction band 100 to a second end 110p of the body 110 (e.g., such as being crimped thereto or otherwise fixed, such as by adhesive or welding). In some embodiments, the stopper member 108 and the body 110 may be a one molded or a comolded component, in contrast with being separately formed and then joined together. In some embodiments, a device may exclude the stopper members 108 (e.g., a device having a fixed ring 104). A third attachment member 103 extends from the second end 100p of the traction band 100. In embodiments, the third attachment member 103 may extend substantially along the longitudinal axis l and outward from the second end 100p of the traction body 100.

The attachment members 101, 102, 103 are loops/hoops that may be engaged by distal ends of medical devices or engaged by fasteners. Although loops/hoops are depicted, various other arrangements may be used such as hooks, anchors, knots, barbs, eyelets, clips, a combination thereof, or the like, reference being made herein to any such term without intent to limit. In various embodiments, an attachment member may comprise a polymer strand (e.g., polypropylene, polyester, nylon, polyethylene, elastic polymers including thermoplastic elastomer (TPE), polyisoprene, silicone, and/or the like), a metal wire (e.g., stainless steel, titanium, cobalt-chrome, nitinol, and/or the like), and/or a natural fiber (e.g., cotton, wool, silk, and/or the like). In some embodiments, e.g., where the body 110 is not included, one or more, or all, of the first, second, and third attachment members may be affixed directly to the band 100, or may be integral to the band 100, such that the shape of the attachment members (e.g., loops) may be incorporated into the shape of the band 100. For example, with reference to FIG. 1, in embodiments, the band 100 may be configured without the body 110 and have the loops of the attachment members 101, 102, 103 as extensions of and/or integral with the band 100, in the arrangement shown with the attachment members 101, 103 as part of band 100 arranged parallel to the longitudinal axis 1 and the attachment member 102 perpendicular or, alternatively, the attachment member 102 could be arranged parallel to the longitudinal axis 1, along the length of the body 110, similar to the attachment members 101, 103. With respect to the foregoing embodiments, and other embodiments, more than three attachment members may be arranged along the band 100, with or without body 110 included, and with one or more of the attachment members between end attachment members (e.g., the attachment members 101, 103) being fixed, slidable, and/or integral with respect to band 100.

A series of protrusions 106 are disposed on the body 110. The protrusions 106 extend substantially radially away from the longitudinal axis 1 along the length of the traction band 100. The protrusions 106 extend radially away from a longitudinal axis 1 extending along the length of the band a number of degrees α that may be, e.g., about 10°, about 15°, about 30°, about 45°, about 60°, about 90°, or the like, or any angle degree in between. The protrusions 106 are arranged circumferentially about the body 110 and about the longitudinal axis 1 of the traction band 100. The protrusions 106 are arranged in rows and columns such that the protrusions 106 are located at varying lengths along the longitudinal axis 1 and at varying arc lengths about a circumference of the body 110. In some embodiments, the protrusions 106 may be shaped differently than the angled substantially cylindrical protrusions 106 shown in FIG. 1 and may correspond, or complement, the attachment members 101, 102, 103, e.g., hooks, loops, ribs, apertures, or the like, for attachment. In embodiments, the protrusions 106 may be disposed uniformly on the body 110, e.g., each extending at the same angle and configuration. In some embodiments, the protrusions 106 may be disposed non-uniformly on the body 110, e.g., extending in differing angles, lengths, configurations, orientations, etc. In some embodiments, at least one protrusion 106 may extend in a first direction, and at least another protrusion 106 may extend in a second direction substantially opposite the first direction. In some embodiments, the protrusions 106 may be shaped and arranged such that some extend perpendicular to the body 110, some extend proximally and some extend distally, with protrusions having different orientations being arranged along the length and about the circumference of the body 110, so that the user has different choices of protrusion to which an attachment member may be engaged. Such choices may be dependent on desired tension, angle, etc.

Figure 2A:
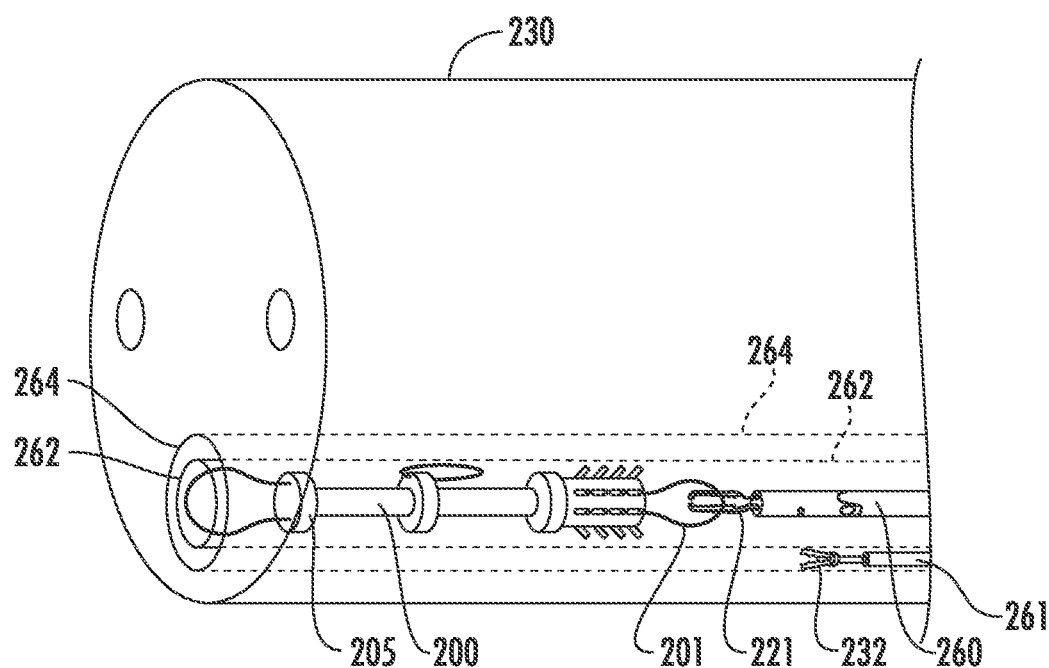
FIG. 2A illustrates the tissue traction device of FIG. 1 within an endoscope for delivery, in accordance with an embodiment of the present disclosure.

Referring to FIG. 2A, a traction device 205 is illustrated according to an embodiment of the present disclosure including a traction band 200 and a first attachment member 201 engaged by a first clip 221. The first clip 221 may be attached to a distal end of a delivery catheter 260 and can be preloaded with the first clip 221 engaged with the first attachment member 201. The delivery catheter 260 and attached traction device 205 can include an outer sheath 262 that may be part of the delivery catheter 260. The delivery catheter 260 with or without the outer sheath 262 may be delivered through a working channel 264 of an endoscope 230 or through some other introducer sheath or catheter. A grasper tool 232 may be delivered independent of the delivery catheter 260, with or without its own grasper catheter or sheath 261, through the working channel 264 of the endoscope 230, through another independent working channel of endoscope 230, or, if small enough, delivered through a working channel of the delivery catheter 260, while the delivery catheter 260 is within the working channel 264 of the endoscope 230. Alternatively, the traction device 205, first clip 221, and grasper tool 232 may each have their own delivery catheter that may each be delivered through the working channel 264 or multiple work channels of the endoscope 230, one at a time or at the same, or some combination thereof. In some embodiments, a first clip 221 may be deployed in the delivery catheter already coupled to an attachment member of the traction device 205. In such instances, the clip 221 may be fixedly or removably coupled to the attachment member 201, or to the band 200 itself.

Figure 2B:
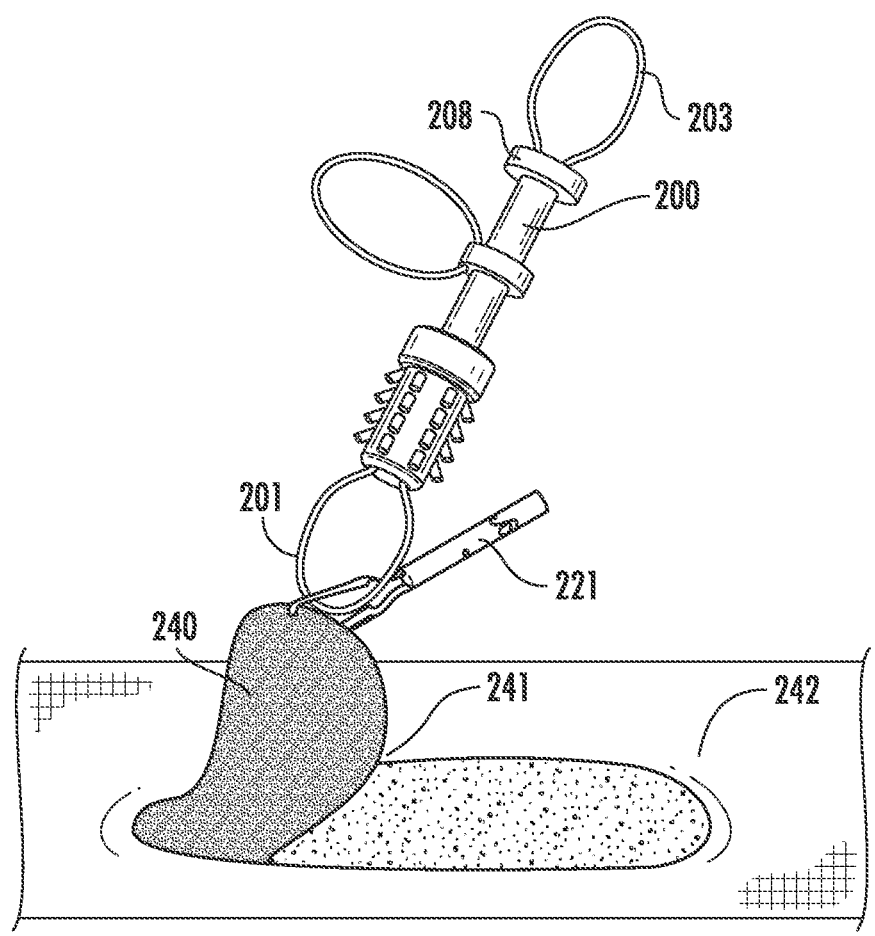
FIG. 2B illustrates the tissue traction device of FIGS. 1 and 2A with a fastener engaging a target tissue, in accordance with an embodiment of the present disclosure.

Referring to FIG. 2B, a tissue retraction system is illustrated according to an embodiment of the present disclosure. A target tissue 240 is shown initially resected from the surrounding tissue 242 (however, the devices and systems described herein may be used prior to an initial resection of the target tissue 240). A medical professional may proceed with a resection procedure by further resecting target tissue 240 away from an area 241 beneath the target tissue 240. However, area 241 may be difficult to visualize and/or access with a resecting tool. To assist with seeing, accessing or otherwise resecting tissue more efficiently, the first clip 221 and the traction device 205 of FIG. 2A may be delivered to the target tissue 240. The first clip 221 may already be engaged, or may be manipulated to engage, the first attachment member 201 of the traction device 205. The first clip 221, engaged with the first attachment member 201, may be manipulated to engage a portion of the target tissue 240.

Figure 2C:
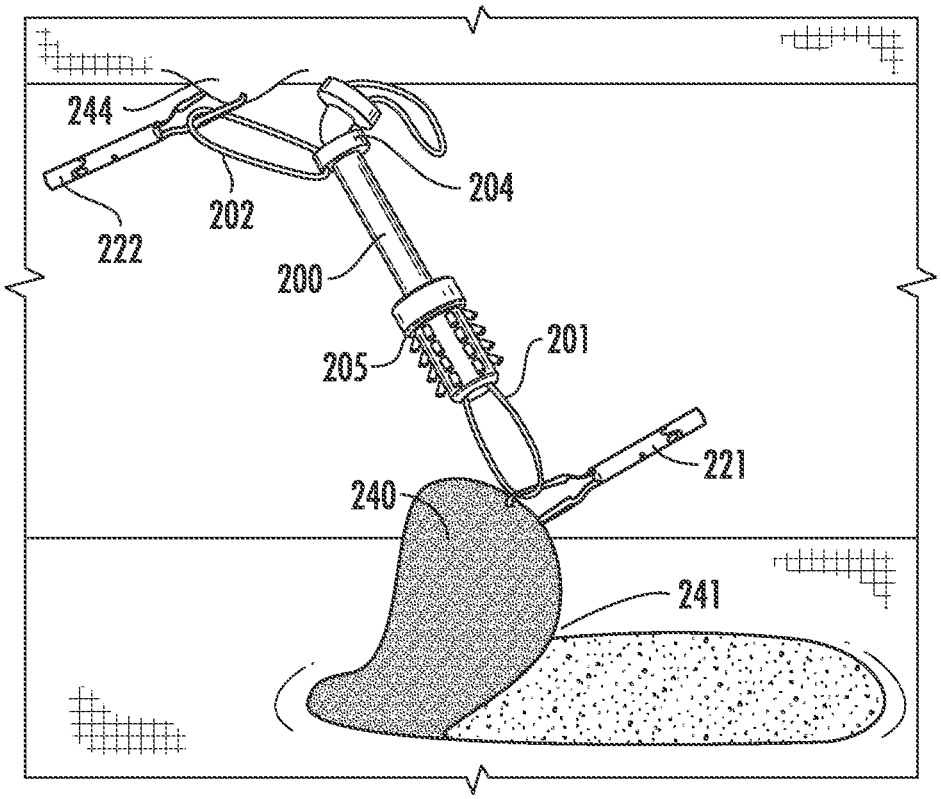
FIG. 2C illustrates the tissue traction device of FIGS. 1 through 2B with another fastener in accordance with an embodiment of the present disclosure engaging an anchoring portion of tissue.

Referring to FIG. 2C, a second clip 222 may be manipulated to engage a second attachment member 202, shown extending from a sliding ring 204 (e.g., extending through the center of the ring 204 to be coupled thereto), of the traction device 205. Alternatively, the second clip 222 may be delivered engaged to the second attachment member 202 and pre-loaded into a working channel of a delivery device rather than being introduced after the first clip 221 engages the target tissue 240. The second clip 222 may be further manipulated while engaging the second attachment member 202 to engage an anchoring tissue 244 of tissue ("anchoring tissue"). Alternatively, the second attachment member 202 may be attached directly to the band 200, or may be integral with the band 200, rather than extending from the sliding ring 204. In such cases, the second clip 222 may engage the second attachment member 202, and may engage the anchoring tissue 244, in a similar manner. The anchoring tissue 244 may be tissue a distance from the target tissue 240, e.g., on an opposite tissue wall, a distance distal or proximal of the target tissue 240, or other separation of tissue. In this manner, if a body (e.g., the body 210 in FIG. 2D) is present as part of the band 200, it may be positioned such that at least one of the protrusions 206 extends towards the target tissue 240. With the first attachment member 201 being fixed to the target tissue 240 by the first clip 221 and the second attachment member 202 being fixed to the anchoring tissue 244, the device 205 may be maintained in tension. The tensioned device may cause the sliding ring 204 to translate along a length of a traction band 200 toward the anchoring tissue 244. The tensioned device 205 tensions the target tissue 240 in a direction toward the anchoring tissue 244 or otherwise positions the target tissue 240 as desired, e.g., revealing an area 241 beneath the target tissue 240 that may allow for a resecting tool to further resect the target tissue 240. The traction band 200 may stretch when the device 205 is in tension, allowing for varying lengths between the target tissue 240 and the anchoring tissue 244. A stopper member 208 (FIG. 2B) may prevent the ring 204 from translating along the traction band 200, over a third attachment member 203, and off of the device 205.

Figure 2D:
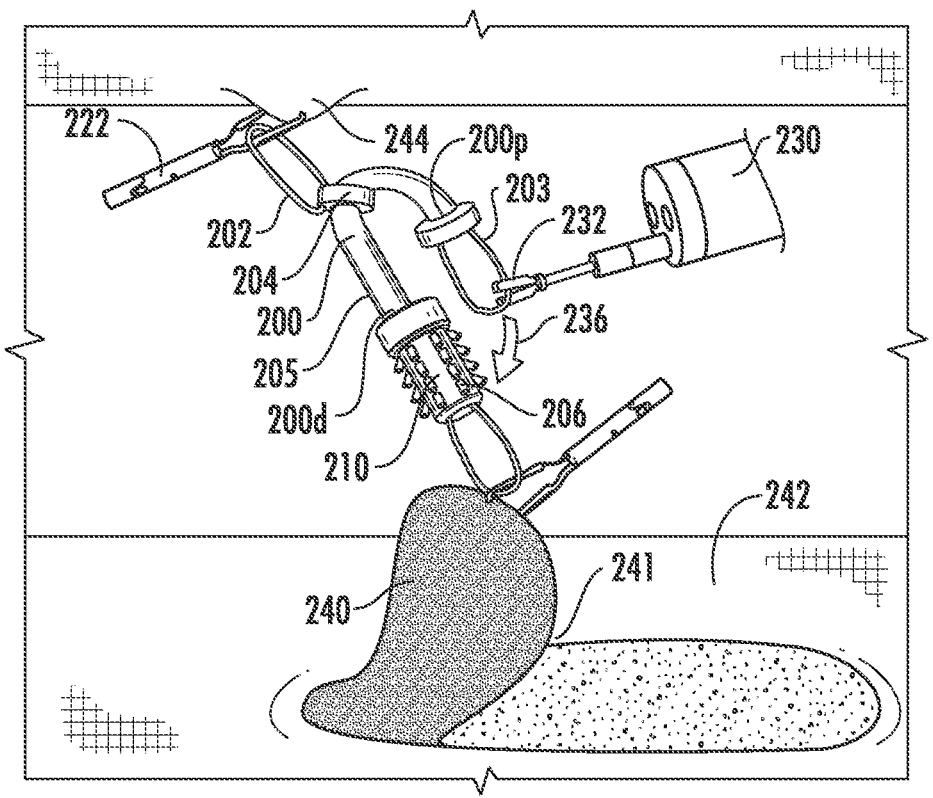
FIG. 2D illustrates the tissue traction device of FIGS. 1 through 2C with an attachment member being moved by a grasping element in accordance with an embodiment of the present disclosure toward a protrusion of the tissue traction device.

Referring to FIG. 2D, a grasper 232 may be extended through a working channel of an endoscope 230 and oriented toward the device 205. The grasper 232 may be manipulated to engage a third attachment member 203 extending from the second end 200p of the traction band 200. The grasper 232 engaging the third attachment member 203 may be manipulated in a direction 236 toward body 210 at a first end 200d of the traction band 200 (e.g., in the general direction of the arrow 236). As the grasper 232 manipulates the third attachment member 203 and the second end 200p toward a protrusion 206 of the body 210, the traction band 200 may stretch and/or extend through the ring 204, the ring 204 being substantially fixed to the anchoring tissue 244 by the second attachment member 202 and the second clip 222, acting as a pivot point. For example, the ring 204 may act as a simple machine pulley with the traction band 200 translating through the ring 204. As the traction band 200 is extended through the ring 204 and/or as the traction band 200 is folded such that the second end 200p is manipulated toward the first end 200d of the traction band 200, a length of the device 205 from the target tissue 240 to the anchoring tissue 244 is shortened. The shortened length of the device 205 may result in increased pull or traction on the target tissue, which lifts the target tissue 240 further away from the surrounding tissue 242 and reveals, or more clearly reveals, a larger, additional and/or different area 241 for a resecting tool to access for further resecting the target tissue 240, as compared to the beginning of the resection procedure.

Figure 2E:
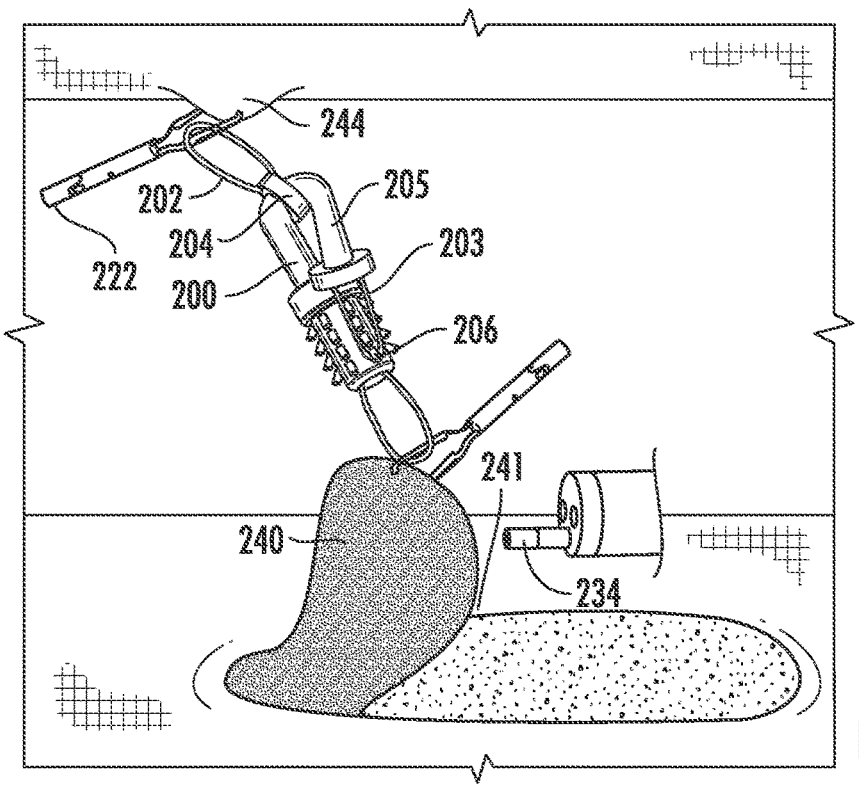
FIG. 2E illustrates the tissue traction device of FIGS. 1 through 2D with an attachment member engaged with a protrusion of the tissue traction device.

Referring to FIG. 2E, the third attachment member 203 is engaged with one of the protrusions 206, e.g., by looping the third attachment member 203 over the selected protrusion 206. As mentioned, at least one of the protrusions 206 extends radially outward at an angle and is positioned to extend towards the target tissue 240 to allow for the third attachment member 203 to catch and hold the selected protrusion 206. This configuration temporarily locks the traction band 200 in the stretched and/or folded configuration through the ring 204, maintaining a shortened length of the device 205 (compared to a longer length of the device 205, e.g., in FIG. 2C). This shortened length of the device 205 maintains the distance between the target tissue 240 and the anchoring tissue 244 and maintains the exposed area 241 for access by a resecting tool 234 for further resection of the target tissue 240. The third attachment member 203 may be further manipulated (e.g., by a grasper 232 of FIG. 2D) to adjust the length of the traction band 200 and the length of the device 205. For example, the third attachment member 203 may be manipulated e.g., by a grasper or other tool, to disengage from one protrusion 206 in order to engage another protrusion 206. As another example, the third attachment member 203 may be manipulated to be disengaged from a protrusion 206 and released such that the third attachment member 203 is not engaged by anything, releasing tension in the traction band 200 and allowing the traction band 200 to unfold, unstretch, and/or translate through the ring 204 such that the length of the device 205 between the target tissue 240 and anchoring tissue 244 increases and tension from the device 205 applied to the target tissue 240 decreases.

Figure 3A:
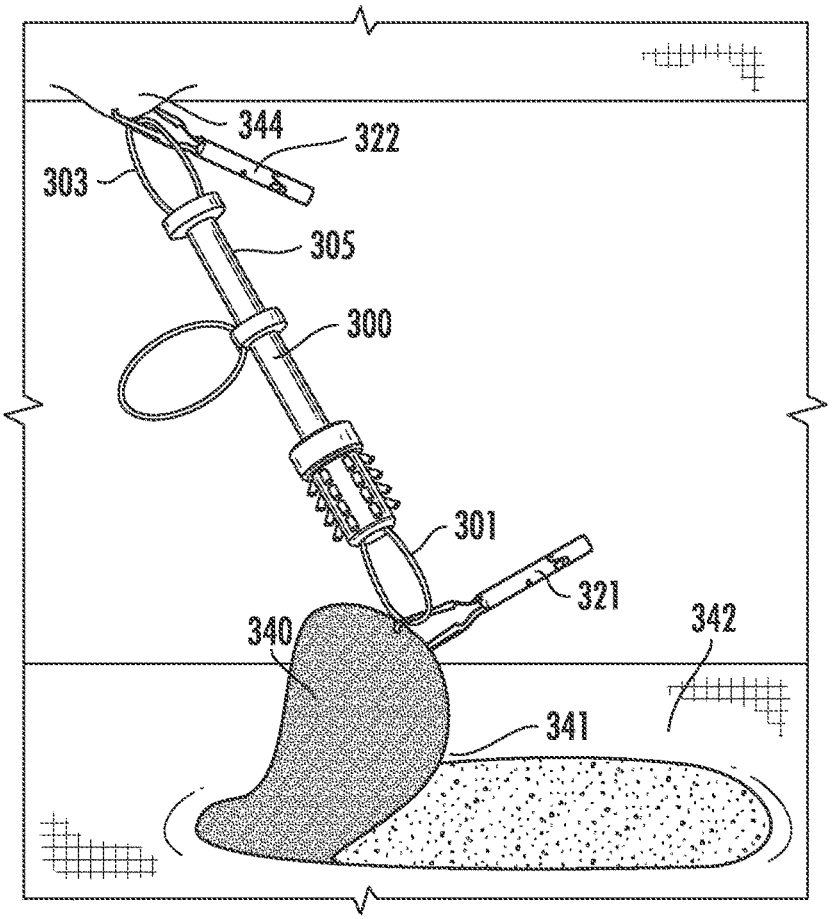
FIG. 3A illustrates the tissue traction device of FIG. 1 fixed to a target tissue and an anchoring tissue by fasteners, and tissue being resected, in accordance with an embodiment of the present disclosure.

Referring to FIG. 3A, a tissue retraction system is illustrated according to an embodiment of the present disclosure. A device 305 is fixed to a target tissue 340 that is shown initially resected away from the surrounding tissue 342, and the device 305 is fixed to an anchoring tissue 344. It is also understood that the target tissue 340 may be unresected when the device 306 is attached, e.g., prior to a dissection procedure. A first attachment member 301 is engaged by a first clip 321 that is also engaging the target tissue 340. A third attachment member 303 is engaged by a second clip 322 that is also engaging the anchoring tissue 344. A medical professional may proceed with a resection procedure by further resecting the target tissue 340 at an area 341 beneath the target tissue 340.

Figure 3B:
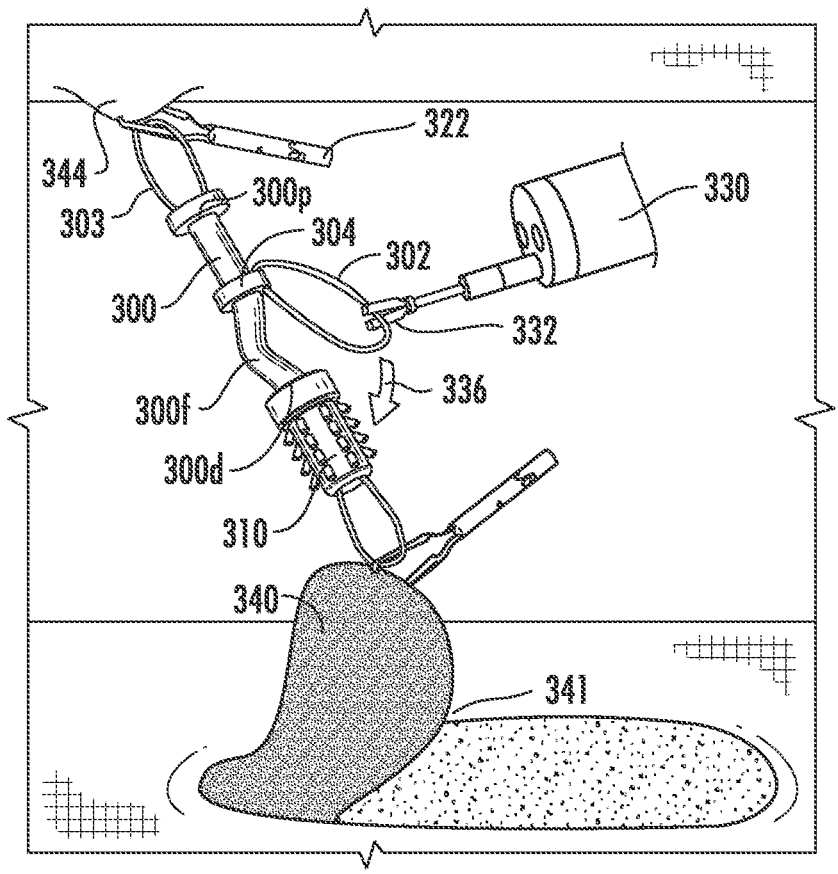
FIG. 3B illustrates the tissue traction device of FIGS. 1 and 3A with an attachment member being moved by a grasping element toward a protrusion of the tissue traction device, in accordance with an embodiment of the present disclosure.

Referring to FIG. 3B, a length of the device 305 between the target tissue 340 and the anchoring tissue 344 may be shortened to further reveal the area 341 beneath the target tissue 340. A second attachment member 302 is extending from a ring 304 that is fixed to the traction band 300. Although the second attachment member 302 is shown attached to the fixed ring 304 (e.g., extending through the center of the ring 304 to be coupled thereto), with the fixed ring 304 at about a mid-portion along the length of the traction band 300, in various embodiments the ring 304 may be fixed to any point along the traction band 300. Alternatively, the second attachment member 302 may instead extend from the second end 300p of the traction band 300 rather than the ring 304. A grasper 332 and second attachment member 302 may be manipulated toward a body 310 at a first end 300d of the traction band 300 (e.g., in the general direction of arrow 336). As the grasper 332 manipulates the second attachment member 302 and the ring 304 toward a protrusion 306 of the body 310, the traction band 300 may fold along a length 300f of the traction band 300 that is between the ring 304 and the body 310. As the traction band 300 is folded, the second end 300p is moved closer to the first end 300d of the traction band 300, and a length of the device 305 from the target tissue 340 to the anchoring tissue 344 is shortened. The shortened length of the device 305 may result in increased pull on the target tissue, which lifts the target tissue 340 further away from the surrounding tissue 342 and reveals, or more clearly reveals, a larger, additional and different area 341 for a resecting tool to access for further resecting the target tissue 340, as compared to the beginning of the resection procedure.

Figure 3C:
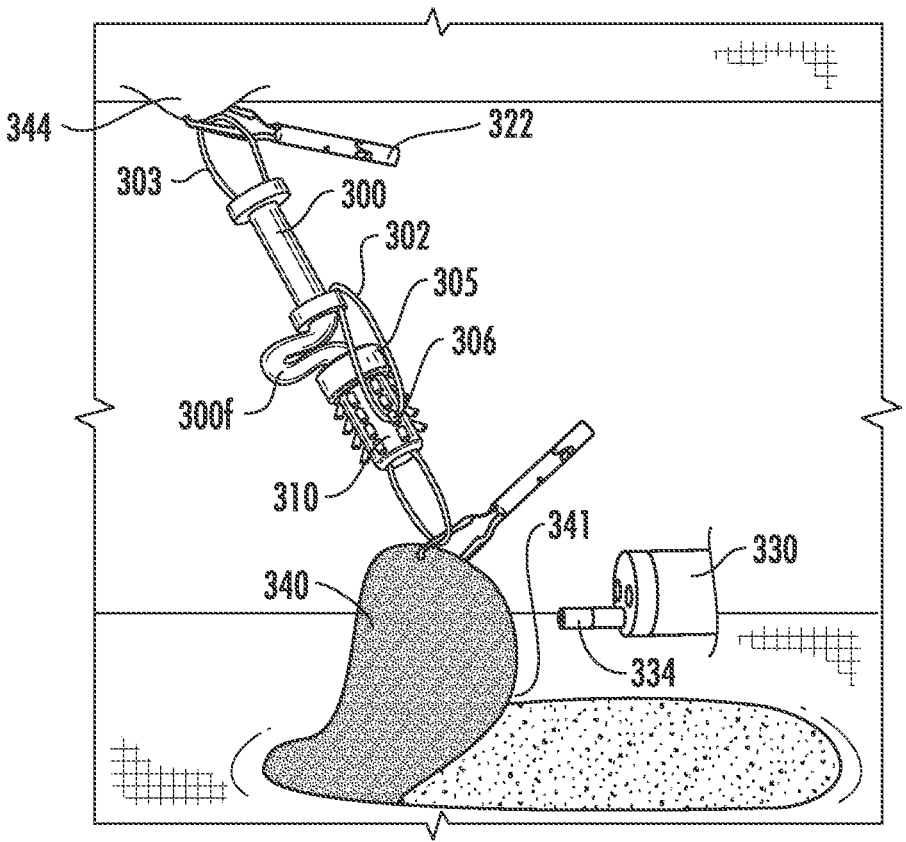
FIG. 3C illustrates the tissue traction device of FIGS. 1, 3A, and 3B with the attachment member of FIG. 3B engaged with the protrusion of the tissue traction device.

Referring to FIG. 3C, the second attachment member 302 is engaged with one of the protrusions 306 of the body 310. This configuration temporarily locks the traction band 300 in the folded configuration (i.e., with the length 300f of the traction band 300 folded), maintaining a shortened length of the device 305 (compared to a longer length of the device 305, e.g., in FIG. 3A). This shortened length of the now locked device 305 maintains the distance between the target tissue 340 and the anchoring tissue 344 such that the exposed area 341 may be accessed by a resecting tool 334 carried by the endoscope 330 for further resection of the target tissue 340. The second attachment member 302 may be further manipulated (e.g., by a grasper 332 of FIG. 3B) to adjust the length of the traction band 300 and the length of the device 305. For example, the second attachment member 302 may be manipulated to disengage from one protrusion 306 and engage another protrusion 306. As another example, the second attachment member 302 may be manipulated to disengage from a protrusion 306 and released such that the second attachment member 302 is not engaged by anything, releasing tension in the traction band 300 and allowing the traction band 300 to lengthen such that the length of the device 305 between the target tissue 340 and anchoring tissue 344 increases.

Referring to FIG. 3D, alternatively, rather than the second attachment member 302 engaging a protrusion 306, the second attachment member 302 may be engaged by a third clip 323. The third clip 323 engaging the second attachment member 302 may also engage a second anchoring portion of tissue 346 ("second anchoring tissue"). The third clip 323 fixes the second attachment member 302 to the second anchoring tissue 346, causing the second attachment member 302 to move the fixed ring 304, and thereby the traction band 300, toward the second anchoring tissue 346. Together, the first clip 321 engaging the first attachment member 301 and the target tissue 340, the second clip 322 engaging the third attachment member 303 and the anchoring tissue 344, and the third clip 323 engaging the second attachment member 302 and second anchoring tissue 346 shortens a length of the device 305 between the target tissue 340 and the anchoring tissue 344 and the second anchoring tissue 346 (when compared to, e.g., the length of the device 305 in FIG. 3A). This shortened length of the device 305 may result in increased pull on the target issue, which lifts the target tissue 340 further away from the surrounding tissue and reveals, or more clearly reveals, a larger, additional and/or different area 341 for the resecting tool 334 and endoscope 330 to access. Use of two anchoring tissue positions may also allow for manipulating the angle of pull that the second attachment member 302 places on the first clip 321 and the target tissue 340. In some embodiments, with more than one anchoring tissue position, a device may alternatively employ a sliding ring or no ring at all, the attachment member 302 in the latter case being fixed directly to the band 300, or made an integral part of the band 300, as described above. In these and other cases, body 310 may not be used.

In various embodiments, an overtube may be provided over the traction band. The overtube may be coaxial to the traction band, and may be freely movable axially and/or rotationally with respect to the traction band. The overtube may have a diameter larger than the traction band, such that the overtube is movable with respect to the traction band when the traction band is in an unstretched, or relaxed, state. Such overtube may be useful in providing a rigid length to the traction device and/or to facilitate smooth movement of the traction band within the delivery sheath, such as the outer sheath 262 illustrated in FIG. 2A, or any other passageway or lumen through which the traction device is passed. Referring to FIGS. 4-7, a segmented overtube 470, 570, 670, 770 may be provided over a traction band 400, 500, 600, 700 of a device 405, 505, 605, 705. One or more attachment members 404, 504, 604, 704 may be coupled to at least one of the overtube segments 474, 574, 674, 774 (only one segment of the multiple segments being labeled for the sake of simplification) of the segmented overtube 470, 570, 670, 770. In some embodiments, an attachment member may be coupled to more than one or each segment of the segmented overtube 470, 570, 670, 770.

Figure 6:
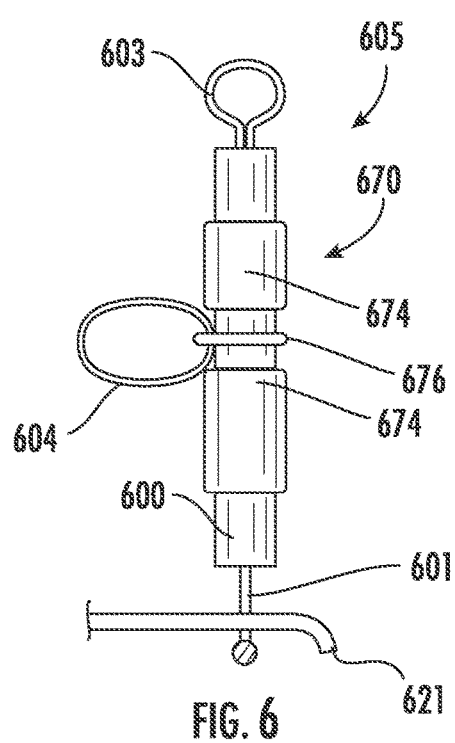
FIG. 6 illustrates an embodiment of a tissue traction device similar to the tissue traction device of FIGS. 4 and 5, but showing a third embodiment of an attachment member, in accordance with the present disclosure.
Figure 7:
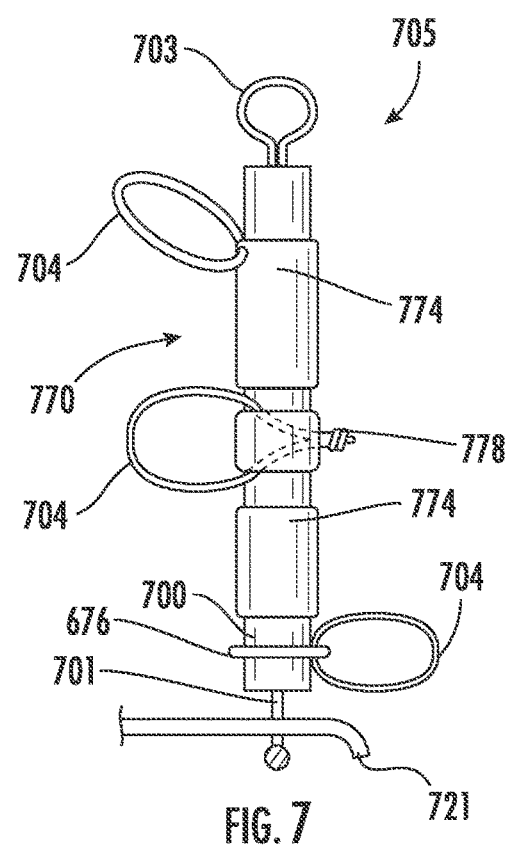
FIG. 7 illustrates an embodiment of a tissue traction device similar to the tissue traction device of FIGS. 4-6, but showing a fourth embodiment of an attachment member, in accordance with the present disclosure.

Referring to FIG. 4, the illustrated overtube segment 474 is a middle segment of the overtube 470, whereas in the embodiment illustrated in FIG. 5, the overtube segment 574 is an end segment of the overtube 570. Other configurations are within the scope of the disclosure, such as illustrated in FIG. 7. As an alternative to coupling an attachment member to an overtube segment, an attachment member 604 may be coupled with a ring 676, as illustrated in FIG. 6. The ring 676 may be rotatably coupled or positioned over the traction band 600. As illustrated, the ring 676 is positioned between two overtube segments 674. However, it will be appreciated that a ring 676 may be provided with or without an overtube 670. Various arrangements of overtube segments and/or rings are within the scope of the present disclosure, the illustrated embodiments not limiting the present disclosure. It will be appreciated that various configurations of segmented overtubes are within the scope and spirit of the present disclosure and are not limited by the examples illustrated in the drawings, the provision of a segmented overtube being understood to allow for addition of one or more attachment members between the ends of the traction band 400, 500, 600, 700 thereby allowing for a variety of tissue clipping configurations and degrees of traction which may be applied by the traction device 405, 505, 605, 705. One or more overtube segments may have one or more attachment members coupled thereto. If desired, the overtube (or a segment thereof) may be fixed with respect to the traction device (e.g., adjacent the proximal end of the traction device), such as by crimping (to the traction band or to an end element coupled thereto), adhesive, or other connection known to those of ordinary skill in the art. Such fixing may be helpful in reliably positioning the overtube or segment thereof, such as if the target tissue is positioned above the endo scope. A body with protrusions similar to a body 110, 210, 310 as described above may be used in conjunction with any of the devices 405, 505, 605, 705, or may not be provided.

The traction device 405, 505, 605, 705 and the attachment member 404, 504, 604, 704 of any or all of the embodiments of FIGS. 4-7 may be used in a manner similar to the manner in which the traction device 305 with the attachment member 302 of FIG. 3D is used. In particular, a first attachment member 401, 501, 601, 701 (shown in cross-section) at a first end of the traction device 405, 505, 605, 705 may be engaged by a clip 421, 521, 621, 721, respectively, that also engages target tissue. The example of a clip 421, 521, 621, 721 is illustrated with a jaw extending through the first attachment member 401, 501, 601, 701. However, other configurations of clips are within the scope of the present disclosure. A third attachment member 403, 503, 603, 703 at a second end of the traction device 405, 505, 605, 705 may be engaged by a second clip (not shown, but which may be any suitable clip, such as described herein) that also engages first anchoring portion of tissue at a first location ("first anchoring tissue"). If additional traction or tension is desired, or a change in direction of traction or tension is desired, the attachment member 404, 504, 604, 704 may be engaged by a third clip (not shown, but which may be any suitable clip, such as described herein) that also engages a second anchoring portion of tissue at a second location ("second anchoring tissue") which may be spaced apart from the first anchoring tissue. Similar effects and benefits as described with respect to FIG. 3D may be achieved, reference being made to such description above for the sake of brevity and without intent to limit. It will be appreciated that with any of these embodiments, the additional angles at which traction or tension may be applied may be advantageous during performance of a procedure on the target tissue, such as resection or dissection of the target tissue, allowing for improved manipulation of the tissue and/or greater degrees of freedom in manipulating tissue such as fibrotic tissue which may be easier to move in certain directions over other directions.

It will be appreciated that the attachment members 404, 504, 604, 704 may be coupled to an overtube segment 474, 574, 774 or a ring 676 in a variety of manners within the scope of the present disclosure. For instance, in some embodiments, such as illustrated in FIG. 4, the attachment member 404 may be coupled to the overtube segment 474 by being looped therethrough. Similarly, in some embodiments, such as illustrated in FIG. 6, the attachment member 604 may be passed through the center of a ring 676 to be coupled with the device 605. If desired, in addition to being passed through the interior passage of an overtube segment, as illustrated in FIG. 7, a portion of the attachment member may be passed from within an overtube segment 774 through an aperture in the wall of the overtube segment 774, and a thickened region 778 (such as a crimp or knot or welding of ends of the element forming the looped attachment member, etc.) may be formed to maintain such portion outside the overtube segment 774 with a portion of the attachment member passing through the aperture in the wall of the overtube segment 774. Alternatively, in some embodiments, such as illustrated in FIG. 5, the attachment member 504 may be coupled to the segment 574 by being attached through an aperture in the wall of the overtube segment 574. It will be appreciated that the position of the aperture may be varied as desired. It will further be appreciated that any of the above-described manners of coupling an attachment member and overtube segment may be applied to any of the embodiments of FIGS. 4-7, as illustrated by way of non-limiting example in FIG. 7. It will further be appreciated that manners of coupling an attachment member 404, 504, 604, 704 to an overtube segment 474, 574, 774 or a ring 676 are applicable to the above-described attachment members 101, 102, 103, 201, 202, 203, 301, 302, 303 to a component of a respective traction device 105, 205, 305 as well. The attachment members 101, 103, 201, 203, 301, 303 at the ends of the traction device 105, 205, 305 may alternatively/additionally be coupled via overmolding/embedding into a component at the end of the traction device 105, 205, 305; inclusion of a feature on the attachment member that provides and interference fit with a components at the ends of the traction device; or by adhesive (e.g., adhering to the traction band 100, 200, 300). For instance, an attachment member 101, 103, 201, 203, 301, 303 may be formed with a knot or crimp or other expansion area passed within the interior of the body 110, 210, 310, and held therein by a narrowing within the body 110, 210, 310 (e.g., a narrowed passageway).

Figure 8:
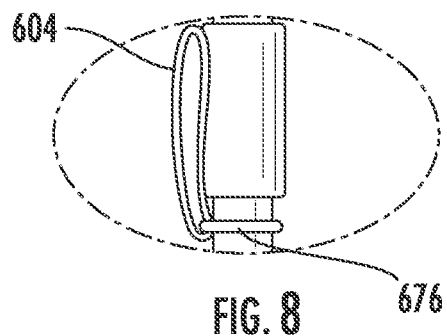
FIG. 8 illustrates a portion of the tissue traction device of FIG. 6 with the attachment member lying substantially flat.

It may be desirable for the attachment member to lie substantially flat with respect to the overtube segments 474, 574, 674, 774, such as during delivery within the outer sheath 262 or the delivery catheter 260. Referring to FIG. 8, showing an isolated section of the traction device 605 of FIG. 6, the attachment member 604 may lie substantially flat over an overtube segment 674 of the segmented tube 670 adjacent the element to which the attachment member 604 is coupled (in this case, ring 676). Alternatively, the attachment member 604 may lie substantially flat tucked within the adjacent overtube segment 674. It will be appreciated that an attachment member 404, 504, 704 coupled to an overtube segment 474, 574, 774 as in FIG. 4 or FIG. 5 or FIG. 7, may similarly lie flat with respect to the overtube segment to which the attachment member 404, 504, 704 is coupled, or with respect to an adjacent overtube segment (adjacent the overtube segment to which the attachment member 404, 504, 704 is coupled).

In various embodiments, a traction band may comprise a compliant or semi-compliant material (e.g., thermoplastic elastomer (TPE), polyethylene terephthalate (PET), elastic polymers, rubbers, plastics, etc.). The traction band may be an elongate cylindrical tube and may be formed hollow or solid.

In various embodiments, a body may comprise non-compliant, semi-compliant, or compliant material (e.g., TPE, PET, elastic polymers, rubbers, plastics, metal, metal alloys, etc.). A traction band may be over molded to a body and/or a stopper member. A body may be injection molded. A body may have apertures at one or both ends of the body for attachment members. A body may have a greater tensile strength than a traction band such that it can withstand an attachment member engaging and pulling on a protrusion of the body. A stopper member may be crimped onto a traction band and/or a body. A body and/or stopper member may include a suture looped or tied to the body and/or stopper member that may be used as a tether for keeping track of the device in a patient or for manipulating the device.

In various embodiments, an attachment member may comprise a compliant or semi-compliant material (e.g., TPE, PET, elastic polymers, rubbers, plastics, etc.). An attachment member may comprise various shapes, e.g., a loop, a hook, an anchor, a barb, an eyelet, a clip, or the like. The attachment member may be a metallic, plastic, braided or any other material that is capable of being formed in the desired shape. A strand of polymer material may be made into a looped attachment member by melting and joining ends of the material. Ends of the attachment member may be joined by a crimp joint or the like. The attachment members may be fixed to another element or component or capable of freely rotating relative to the element or component with which it is coupled. An attachment member may have a material strength configured to fail at a pre-determined load as a safety feature to limit an amount of tension in the attachment member, the device, and the surrounding tissue. One or more attachment members may be visually marked such that the attachment members are visually distinguishable with respect to other attachment members. For example, the attachment members may vary in colors, patterns, or radiopacity such that a medical professional can easily identify a particular attachment member meant for fixation to a target tissue, an anchoring tissue, a second anchoring tissue, a protrusion, etc. In various embodiments, such as those with relatively flexible attachment members, the attachment member may be positioned to lie substantially flat against the device 105, 205, 305, 405, 505, 605, 705 during delivery, such as described above with respect to FIG. 6. In some embodiments, once the device 105, 205, 305, 405, 505, 605, 705 reaches the target tissue, the attachment member may be released to extend away from the device 105, 205, 305, 405, 505, 605, 705 to provide easy access to the attachment member while coupling a clip thereto within the body. One manner of maintaining an attachment member in a delivery configuration, such as substantially flat along the device, is illustrated in FIG. 8.

In various embodiments, some steps of assembling a tissue traction device may occur outside of the patient's body, while other steps involved in assembling the tissue traction device may occur within the patient. The steps described herein do not necessarily occur in a specific order and/or timing.

The medical instruments used with various embodiments of the devices, systems, and methods herein are not limited to those illustrated and discussed but may include a variety of medical instruments (e.g., ablative elements, biopsy needles, injection needles, scissors, graspers, clips, etc.).

In various embodiments, an access area beneath and about a target tissue to be resected by a medical professional may be visualized. Visualization may be optical, fluoroscopic, ultrasonic, etc. The visualization of the area beneath and about the target tissue may not be adequately revealed for the medical professional to manipulate a medical instrument to the access area to resect the target tissue. The medical professional may deliver and deploy a tissue retraction system to the target tissue and an anchoring tissue at a length and/or at a tension that reveals the access area for the procedure. The medical professional may adjust the length or tension of the system based on visualization of the target tissue or access area.

In various embodiments, an attachment member may be engaged with a variety of different fasteners configured to engage a tissue traction device to a tissue, such as a clip, an anchor, a screw, a pin, or the like. One of the attachment members could be acquired by or permanently coupled to a deployable clip. Once acquired by an attachment member, or if already coupled, the clip would be deployed to the tissue flap created along the target tissue margin. One or more clips could be used to fix the attachment member and the traction band to the target tissue.

In various embodiments, a clip is configured in any desired manner to couple an attachment member to another element, such as a tissue traction device, or tissue of a patient. In various embodiments, a clip contemplated for use with a tissue traction device may include a biased-open configuration to move to a closed/clamped configuration upon actuation by a handle assembly. In addition, or alternatively, a tissue clip contemplated for use with the disclosed tissue traction device may include a biased-closed configuration configured to move to an open configuration upon actuation of a distal end effector (e.g., squeezing) by a proximal handle assembly. In addition, or alternatively, fasteners other than detachable/releasable tissue clips may be sued to secure/engage the attachment members of the disclosed tissue traction device to the wall of a body lumen, such as non-repositionable clips. Examples of fasteners may include, but are not limited to, those described in U.S. Patent Application Publication 2020/0360023, filed May 13, 2020, and titled "Tissue Clip Devices, Systems, And Retraction Methods"; U.S. Patent Application Publication number 2020/0129181, filed Oct. 30, 2019; U.S. Patent Application Publication number 2020/0129181, filed Mar. 19, 2018; and U.S. Pat. No. 8,062,311, issued Nov. 22, 2011, and titled "Endoscopic Hemostatic Clipping Apparatus", all of which are herein incorporated by reference in their entireties and for all purposes. Other features and aspects of these patents and patent applications, as well as U.S. Provisional Patent Application No. 62/848,815, filed on May 16, 2019, and titled "Tissue Traction Bands And Methods Of Use Thereof"; and U.S. Pat. No. 11,464,520, issued Oct. 11, 2022, and titled "Tether Traction Systems And Methods Of Use Thereof", which applications are herein incorporated by reference in their entireties for all purposes, may complement devices and methods of the present disclosure and may be used therewith.

Figure 9A:
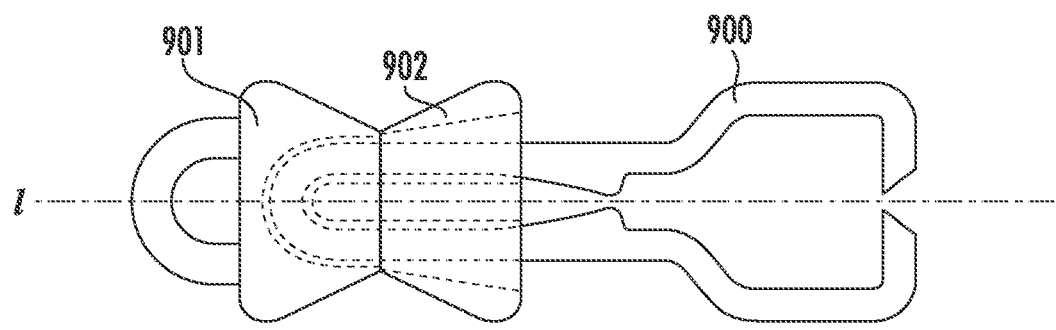
FIG. 9A illustrates an example of a tissue clip, in a closed configuration, which may be used with embodiments of the present disclosure.
Figure 9B:
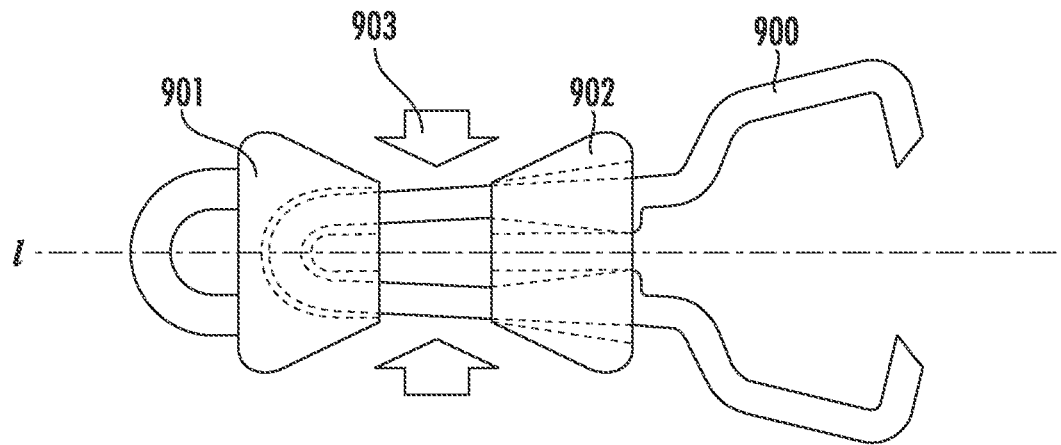
FIG. 9B illustrates the tissue clip of FIG. 9A in an open configuration.

Referring to FIGS. 9A and 9B, an example tissue clip disclosed in above-referenced U.S. Patent Publication 2020/0129181 and that may be used with an embodiment of the present disclosure is illustrated. The illustrated tissue clip includes first and second members 801, 802. Two clip arms 800 extend from the first member 801 and are received within the second member 802. The clip arms 800 are movable between a closed configuration as depicted in FIG. 9A, in which the arms 800 are positioned toward each other, and an open configuration as depicted in FIG. 9B, in which the arms 800 are separated away from each other. The first and second members 801, 802 may each be displaced relative to each other along a longitudinal axis l into the open configuration in response to an application of a compressive force 803.

In various embodiments, a method of retracting tissue may include delivering a tissue traction device to a target tissue. A first attachment member extending from a first end of the tissue traction device may be attached to the target tissue. A second attachment member extending from a length of the tissue traction device may be attached to an anchoring portion of tissue. The target tissue may be resected. A third attachment member extending from a second end of the tissue traction device may be engaged to a first protrusion extending from the tissue traction device. A tension, and/or length of the tissue traction device, applied by the tissue traction device to the target tissue may be adjusted. The third attachment member may be moved from the first protrusion to a second protrusion extending from the tissue traction device. The first attachment member and the target tissue may be engaged with a first fastener. The second attachment member and the anchoring portion of tissue may be engaged with a second fastener. An area of access beneath the target tissue may be visualized and a position of the third attachment member may be adjusted based on the visualized area of access.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A tissue traction device, comprising:
    a stretchable traction band having a first end, a second end, a length therebetween and extending along a longitudinal axis;
    a first attachment member extending from the first end of the traction band;
    a second attachment member configured to be engaged with tissue by a tissue fastener, and extending from a ring encircling and slidably disposed on the traction band between the first end and the second end of the traction band; and
    a third attachment member extending from the second end of the traction band;
    wherein at least one of the first attachment member, the second attachment member, and the third attachment member is in the form of a loop.

2. The tissue traction device of claim 1, further comprising a tissue fastener, the second attachment member configured to be attached to the tissue fastener to be engaged with tissue by the tissue fastener.

3. The tissue traction device of claim 2, further comprising: a first stopper disposed about the traction band between the ring and the first end, the first stopper configured to prevent the ring from translating along the length of the traction band to the first attachment member; and a second stopper disposed about the traction band between the ring and the second end, the second stopper configured to prevent the ring from translating along the length of the traction band to the third attachment member.

4. The tissue traction device of claim 1, wherein the second attachment member is configured to be engaged by a tissue fastener such that the tissue fastener is manipulable while engaged with the second attachment member to reversibly engage the second attachment member with tissue.

5. The tissue traction device of claim 1, further comprising a body disposed at the first end of the traction band and at least one protrusion disposed on the body, wherein the protrusion extends at an angle radially away from the longitudinal axis of the traction band.

6. The tissue traction device of claim 5, further comprising at least a first and second protrusion, the second protrusion disposed on the body between the first protrusion and a first end of the body.

7. The tissue traction device of claim 1, wherein each of the first attachment member, the second attachment member, and the third attachment member is in the form of a loop.

8. The tissue traction device of claim 1, wherein at least one of the first attachment member, the second attachment member, and the third attachment member further comprises a visual indicator that is visually distinguishable from the remaining members.

9. The tissue traction device of claim 1, wherein the tissue fastener comprises a clip with a pair of jaws movable with respect to each other, and the second attachment member includes a loop engageable by at least one of the jaws of the clip.

10. A tissue traction system, comprising:
a tissue traction device comprising:
   a traction band having a first end, a second end, and a length therebetween extending along a longitudinal axis;
   a body extending circumferentially around the longitudinal axis of the traction band;
   a plurality of protrusions disposed circumferentially around the body and extending radially outwardly from the longitudinal axis of the traction band;
   a first attachment member extending from the first end of the traction band;
   a second attachment member extending from the traction band; and
   a third attachment member extending from the second end of the traction band;
wherein at least one of the second attachment member or the third attachment member is shaped to be capable of being held in an engaged position on at least one of the plurality of protrusions on the body to adjust the length of the traction band.

11. The tissue traction system of claim 10, further comprising a grasping tool configured to engage and move the third attachment member into engagement with one of the plurality of protrusions.

12. The tissue traction system of claim 10, further comprising a first tissue fastener configured to reversibly engage the first attachment member with a first target tissue location, and a second tissue fastener configured to reversibly engage the second attachment member with a second target tissue location.

13. The tissue traction system of claim 10, further comprising a third tissue fastener engageable with the third attachment member.

14. The tissue traction system of claim 10, wherein the body is disposed at the first end of the traction band.

15. The tissue traction system of claim 10, wherein:
the tissue traction device is pre-loaded, prior to use, within a delivery catheter and with a tissue fastener engaged with the first attachment member; and
the tissue traction system is configured to deliver the traction band and the first tissue fastener.

16. The tissue traction system of claim 10, further comprising a ring disposed about and positioned along the length of the traction band, the second attachment member extending from the ring.

17. A method of applying traction to tissue, the method comprising:
delivering a tissue traction device to a target tissue;
attaching a first attachment member extending from a first end of the tissue traction device to the target tissue;
attaching, with a tissue fastener, a second attachment member extending from a ring encircling and slidably disposed on the tissue traction device to an anchoring portion of tissue;
performing a procedure on the target tissue; and
adjusting a tension applied by the tissue traction device to the target tissue to retract the target tissue relative to surrounding tissue with respect to which the target tissue has been resected to increase an area of access beneath the target tissue.

18. The method of claim 17, further comprising engaging a third attachment member from a second end of the tissue traction device to a first protrusion extending from the tissue traction device or to another anchoring portion of tissue.

19. The method of claim 18, further comprising moving the third attachment member from the first protrusion to a second protrusion extending from the tissue traction device.

20. The method of claim 17, wherein attaching the first attachment member extending from the first end of the tissue traction device to the target tissue further comprises engaging the first attachment member and the target tissue with a first fastener, and wherein attaching the second attachment member extending from the length of the tissue traction device to the anchoring portion of tissue further comprises engaging the second attachment member and the anchoring portion of tissue with a second fastener.

\* \* \* \* \*